(12) United States Patent
Smith

(10) Patent No.: US 7,108,845 B2
(45) Date of Patent: Sep. 19, 2006

(54) METHODS OF SYNTHESIS AND USE OF RADIOLABELLED PLATINUM CHEMOTHERAPEUTIC AGENTS

(75) Inventor: Suzanne V. Smith, Cronulla New South Wales (AU)

(73) Assignee: Australian Nuclear Science & Technology Organisation, New South Wales (AU)

( * ) Notice: Subject to any disclaimer, the term of this patent is extended or adjusted under 35 U.S.C. 154(b) by 32 days.

(21) Appl. No.: 10/239,363

(22) PCT Filed: Mar. 23, 2001

(86) PCT No.: PCT/AU01/00320

§ 371 (c)(1),
(2), (4) Date: Dec. 10, 2002

(87) PCT Pub. No.: WO01/70755

PCT Pub. Date: Sep. 27, 2001

(65) Prior Publication Data

US 2003/0103896 A1    Jun. 5, 2003

(30) Foreign Application Priority Data

Mar. 23, 2000 (AU) .................... PQ6411

(51) Int. Cl.
A61K 49/00    (2006.01)
(52) U.S. Cl. .............. 424/9.1; 424/1.11; 424/1.65
(58) Field of Classification Search .............. 424/1.11, 424/1.65, 9.1, 1.81, 1.85, 1.89; 556/136, 556/1.37
See application file for complete search history.

(56) References Cited

U.S. PATENT DOCUMENTS

| | | | |
|---|---|---|---|
| 4,177,263 A | 12/1979 | Rosenberg et al. | |
| 4,203,912 A | 5/1980 | Hydes et al. | |
| 4,302,446 A | 11/1981 | Kaplan et al. | |
| 4,310,515 A | 1/1982 | Granatek et al. | |
| 4,322,391 A | 3/1982 | Kaplan et al. | |
| 4,339,437 A | 7/1982 | Rosenberg et al. | |
| 4,451,447 A | 5/1984 | Kaplan et al. | |
| 4,562,275 A | 12/1985 | Speer et al. | |
| 4,594,418 A | 6/1986 | Speer et al. | |
| 4,607,114 A | 8/1986 | Nakayama et al. | |
| 4,687,780 A | 8/1987 | Barnard | |
| 4,696,918 A | 9/1987 | Stoddart et al. | |
| 4,739,087 A | 4/1988 | Speer et al. | |
| 4,863,902 A | 9/1989 | Amagase et al. | |
| 4,871,528 A | 10/1989 | Tognella et al. | |
| 4,892,735 A | 1/1990 | Harrap | |
| 4,943,428 A | 7/1990 | Lucot et al. | |
| 4,946,689 A | 8/1990 | Kaplan et al. | |
| 5,041,579 A | 8/1991 | Nishi et al. | |
| 5,072,011 A | 12/1991 | Abrams et al. | |
| 5,080,904 A | 1/1992 | Iga et al. | |
| 5,104,896 A | 4/1992 | Nijkerk et al. | |
| 5,130,145 A | 7/1992 | Oftebro et al. | |
| 5,143,713 A | 9/1992 | Phillips et al. | |
| 5,158,760 A | 10/1992 | Phillips et al. | |
| 5,194,645 A | 3/1993 | Barnard | |
| 5,244,919 A | 9/1993 | Abrams et al. | |
| 5,272,056 A | 12/1993 | Burrows et al. | |
| 5,393,909 A | 2/1995 | Khokhar et al. | |
| 5,434,046 A | 7/1995 | Enns et al. | |
| 5,434,256 A | 7/1995 | Khokhar et al. | |
| 5,455,270 A | 10/1995 | Kaplan et al. | |
| 5,562,925 A | 10/1996 | Rosenberg et al. | |
| 5,578,590 A | 11/1996 | Grunicke et al. | |
| 5,601,800 A | 2/1997 | Katti et al. | |
| 5,635,493 A | 6/1997 | Vournakis et al. | |
| 5,665,771 A | 9/1997 | Murrer | |
| 5,670,502 A | 9/1997 | Brown | |
| 5,696,131 A | 12/1997 | Baguley et al. | |
| 6,008,395 A | 12/1999 | Kidani | |
| 6,074,626 A | 6/2000 | Order | |

FOREIGN PATENT DOCUMENTS

| | | |
|---|---|---|
| AU | 626189 | 3/1989 |
| AU | 613810 | 11/1989 |
| EP | 0181166 | 5/1986 |
| EP | 0306605 | 3/1989 |
| GB | 2074028 | 10/1981 |
| PL | 182490 | 4/1996 |

OTHER PUBLICATIONS

Benard et al, Cancer Treatment Reports, vol. 67, No. 5, 1983, pp. 457-466.*
Kawai et al, Journal of Labelled Compounds and Radiopharmaceuticals, vol. XXXVI, No. 1, pp. 65-71.*
Howell et al, Radiation Research, vol. 140, pp. 55-62 (1994).*
Baer et al, Int. J. Appl. Radiat. Isotop., vol. 36, No. 3, pp. 181-184 (1985).*
Baer, J. et al. Microscale Synthesis of Anti-Tumor Platinum Compounds Labelled with $^{191}Pt$. Int. J. Appl. Radiat. Isot. vol. 36, No. 3 pp. 181-184 (1985).
Benard P. et al. Whole Body Autoradiographic Study of the Distribution of $^{195m}Pt$. in Healthy and Tumor-Bearing Mice Treating With Labeled Cisplatin[1.] Cancer Treatment Reports vol. 67, No. 5 (May 1983).

(Continued)

Primary Examiner—Dameron L. Jones
(74) Attorney, Agent, or Firm—Banner & Witcoff, Ltd.

(57) ABSTRACT

There is provided a method of synthesis of a radiolabelled platinum chemotherapeutic agent comprising the steps of: converting a metal halide to a radiolabelled platinum halide wherein the radiolabel is a radioisotope of Pt; and synthesizing the radiolabelled platinum chemotherapeutic agent from the radiolabelled platinum halide.

16 Claims, No Drawings

OTHER PUBLICATIONS

Howel, R.W. et al. *Radiotoxicity of Platinum-195m-Labeled trans-Platinum (II) in Mammalian Cells*, Radiation Research 140, 55-62 (1994).

Jackson H. et al. *An Improved Synthetic Procedure For The Preparation of $^{195m}Pt$ Labelled Anti-Tumour Complexes* Journal of Labelled Compounds and Radiopharmaceuticals, vol. 29, No. 10 pp. 1121-1130 (Jun. 25, 1991).

Kataoka, M. et al. *Scintigraphic Study on the Distribution of Radiolabeled cis-Diamminedichloroplatinum (II) in the Tumor-bearing Rabbit: A Comparison between Intra-arterial Injection with Lipiodol and Intravenous Injection*. Radiation Oncology; Radiation Medicine: vol. 11 No. 6. pp. 247-250 (1993).

Kawai, K. et al., *Synthesis of Platinum-195m Radiolabelled cis-Diammine (1.1-cyclobutanedicarboxylato) platinum(II) of High Radionuclidic Purity*, Journal of Labelled Compounds and Radiopharmaceuticals vol. 36 No. 1, 65-71 (Aug. 15, 1994).

Kawai K. et al. *Synthesis of $^{195m}Pt$ Radiolabeled Cis-Diammine (Glycolato) Platinum(II) of High Radionuclidic Purity*. J. Radioanal. Nucl. Chem., Letters 199 (3) pp. 207-215 (1995).

Lange, R.C. et al. *The Antitumor Agent Cis-Pt(NH$_3$)$_2$ Cl$_2$-Distribution Studies and Dose Calculations for $^{193m}Pt$ and $^{195m}Pt$* Section of Nuclear Medicine, Yale University School of Medicine, New Haven, CT, Journal of Nuclear Medicine, vol. 14, No. 4 191-195 (1972).

Lange, R.C. et al. *Synthesis and Distribution of Radiolabeled Antitumor Agent: cis-Diamminedichloroplatinum (II)* Yale University School of Medicine, New Haven, CT. Journal of Nuclear Medicine, vol. 13, No. 5 328-330 (1972).

Leh, F.K.V. et al. *Preparation and Distribution of $^{195}Pt^m$ -Labeled Bleomycin* Radiopharmacy Program, Cancer Hospital and Research Institute, and School of Pharmacy, Los Angeles County, University of Southern California. International Journal of Pharmaceutics, 1 pp. 41-47 (1978).

Litterst, C.L. et al. *Distribution and Disposition of Platinum following Intravenous Administration of cis-Diamminedichloroplatinum(II) (NSC 119875) to Dogs*, Cancer Research vol. 36, 2340-2344, Jul. 1976

Owens, S.E. et al. *In Vivo Distribution Studies of Radioactively Labelled Platinum Complexes; cis-dichlorodiammine platinum(II), cis-trans-dichlorodihydroxy-bis-(isopropylamine) platinum(IV), cis-dichloro-bis-cyclopropylamine platinum(II), and cis-diammine1, 1-cyclobutanedicarboxylate platinum(II) in patients with malignant disease, using a gamma camera*. Cancer Chemotherapy and Pharcamology 14: 253-257 (1985).

Schlesinger, T. et al., *Dosimetry of Pt-195m: CIS-Dichlorodiammine-Platinum(Ii) And Other Platinum Compounds*, Proc. Radiopharm. Dosimetry Symposium 1976, Oak Ridge, TN, pp. 452-461.

Shani J. et al. *Noninvasive Monitoring of Drug Biodistribution and Metabolism: Studies with Intraaerterial Pt-195m-Cisplatin in Humans*, Cancer Research 49, 1877-1881 (Apr. 1, 1989).

Sharma, H. et al. *Blood Clearance of Radioactively Labelled cis-Diammine 1, 1-cyclobutane Dicarboxylate Platinum(II) (CBDCA) in Cancer Patients* Cancer Chemotherapy and Pharmacology 11:5-7 (1983).

Smith, P.H.S. et al. *Distribution and Retention of the Antitumor Agent $^{195m}Pt$-cis-Dichlorodiammine Platinum (II) In Man*. Royal Marsden Hospital and Institute of Cancer Research, Sutton, Surrey, U.K., Journal of Nuclear Medicine, vol. 15, No. 5 349-352 (1974).

Suwa M. et al. *A Microscale Synthesis of a Promising Radiolabelled Antitumor Drug: cis-1,1-cyclobutanedicarboxylato (2R)-2-Methyl-1, 4-butanediamine platinum(II), NK121*. Journal of Labelled Compounds and Radiopharmaceuticals, vol. 31, No. 5 pp. 349-354 (Jan. 6, 1992).

Thatcher N. et al. *Blood Clearance of Three Radioactively Labelled Platinum Complexes: cis-Dichlorodiammine Platinum II, cis, trans-Dichlorodihydroxy-bis-(isopropylamine) Platinum IV, and cis-Dichloro-bis-cyclopropylamine Platinum II, in Patients with Malignant Disease*. Cancer Chemotherapy Pharmacology. 9: 13-16 (1982).

Toth, G. et al. *Production and Examination of the Organ Distribution of Cis-Dichlor-Diammine-Platinum, Labeled with $^{193}Pt^m$* Certified Translation of Hungarian Language, Izotoptechnika Budapest 19 pp. 49-51 (1976) (translation).

Willins, J. D. et al. *Modeling Analysis of Platinum-195m for Targeting Individual Blood-Borne Cells in Adjuvant Radioimmunotherapy*. Department of Medical Physics, Memorial Sloan-Kettering Cancer Center, New York, NY. The Journal of Nuclear Medicine. vol. 36 No. 2 pp. 315-319 (Feb. 1995).

Wolf, W. et al. *$^{195}Pt^m$ A New Radionuclide: Its Application to the Monitoring of Cancer Chemotherapeutic Agents* Recent Advances in Nuclear Medicine Proceedings of the First World Congress of Nuclear Medicine pp. 944-945 Sep. 30-Oct. 5, 1974, Tokyo and Kyoto, Japan.

Wolf, W. et al. *Synthesis of Radiolabeled Platinum Complexes* Radiopharmacy Program, University of Southern California, Los Angeles, CA. Journal of Labelled Compounds and Radiopharmaceuticals, vol. 13, No. 2 p. 183 (1977).

Degner, Maria et al. *Binary Halides of Platinum: Preparation, Thermal Decomposition and Structural Results*. Transition Met. Chem 1. Aug. 11, 1975, pp. 41-47. Germany.

Cohen, Alvin J. et al. *Platinum (II) Chloride*. Inorganic Synthesis. 1960, pp. 209-215, vol. VI. McGraw-Hill Book Company, Inc. United States of America.

Schweizer, A.E. et al. *Thermal Decomposition of Hexachloroplatinic Acid*. Inorganic Chemistry. 1978, pp. 2326-2327, vol. 17. American Chemical Society, United States of America.

Shchukarev, S.A. et al. *Thermal Dissociation of Platinum Halides*. Journal of Inorganic Chemistry. 1956, pp. 17-24, vol. I, No. 1. USSR.

Wöhler, Von L. et al. *Die binären Bromide und Jodide des Platins*. Sep. 1925, pp. 377-386. Chemisches Institut der technischen Hochschule. Germany.

\* cited by examiner

METHODS OF SYNTHESIS AND USE OF RADIOLABELLED PLATINUM CHEMOTHERAPEUTIC AGENTS

This Application claims priority to Australian Patent Application No. PQ 6411 filed Mar. 23, 2000 and PCT/AU01/00320 filed Mar. 23, 2001.

BRIEF SUMMARY OF THE INVENTION

The present invention relates to methods of synthesis of radiolabelled platinum chemotherapeutic agents including radiolabelled cis-platin. The present invention also relates to methods of diagnosis of diseases, methods of therapy of diseases, methods of prognosis of diseases, and methods of assessing the effectiveness of treatment of diseases using radiolabelled platinum chemotherapeutic agents.

BACKGROUND OF THE INVENTION

The treatment of cancer typically requires the optimal sequence of one or more of the effective treatments (e.g. surgery, radiotherapy, and chemotherapy). Patients for whom the disease is at an early stage can frequently be operated on to remove the cancer. In many cancers follow up adjuvant chemotherapy is required for micro-metastatic disease. In others with locally advanced or metastatic disease, cancer control relies on radiotherapy and/or chemotherapy. In cancer therapy, failure to cure the disease generally results from intrinsic or acquired tumour cell resistance to drugs or radiotherapy. In such instances, the treatments become ineffective and survival times for such patients may be considerably reduced. Thus it is important to develop new approaches to cancer which may enhance the cytotoxicity of known chemotherapeutic agents.

The combination of external radiation and chemotherapy has in many instances been reported to have a synergistic effect on therapy. However, combining these two modalities effectively relies on an unending of the mechanisms that lead to the enhanced therapeutic index and the exploitable differences in the properties of tumours and normal tissues.

Platinum based chemotherapeutic agents are used in the treatment of cancers. These agents exert their cytotoxic effect by binding with the DNA of the cancer cell and causing strand breaks, and consequently preventing the cell from dividing further and causing cell death. A number of mechanisms are manifested in in vitro resistance to the chemotherapeutic agents. They are usually manifested in decreased transport of the drug into the cell, thiol inactivation, enhanced DNA repair or a combination of some or all of these mechanisms. There is a need for an effective method to monitor the development of resistance to platinum based chemotherapeutic agents in vivo, and for an effective method for assessing the effectiveness of treatment of diseases such as cancer which are undergoing treatment by administration of a platinum based chemotherapeutic agent.

Cisplatin (cis-dichlorodiammine-platinum(II)) and carboplatin (cis-diammine(1,1-cyclobutanedicarboxylato) platinum(II)) are the two most widely prescribed platinum based chemotherapeutic agents at the present time. Reports have appeared in the literature of the use of radiolabelled cisplatin to assess the biodistribution of cisplatin in animals. However, to date there has been no medical use of radiolabelled platinum based therapeutic agents. The methods whereby radiolabelled cisplatin has hitherto been prepared suffer from a number of disadvantages. They use as their starting point platinum metal which has been enriched in a radio-isotope of platinum by irradiation of platinum metal in a nuclear reactor, typically with neutrons.

Starting with platinum metal, the synthesis of radiolabelled cisplatin is relatively time consuming requiring in the order of 6.5 hours to complete. For radionuclides with half-lives of hours, a few hours' delay in the preparation of radiolabelled cisplatin can lead to significant loss of specific activity, especially as in a production environment this amount of delay may result in product only reaching a patient on the following working day. Such a delay causes significant loss of specific activity of the radioisotope. In this instance, in order for a desired amount of radioactivity to be administered to a patient, the overall dosage of unradiolabelled cisplatin carrier will be increased as the specific activity of the radiolabelled substance decreases. It may then become impractical to administer sufficient of the agent to deliver the desired amount of radioactivity if the specific activity is too low.

By contrast, a significantly shorter synthesis time can permit the distribution of the product and its administration to the patient on the same day as the agent is administered, without the concomitant loss in specific activity.

Furthermore the prior art synthesis of cisplatin from platinum metal exhibits relatively low and variable yields, and is unreliable and may at times give no yield of the desired product. Low yield of radiolabelled cisplatin or other radiolabelled chemotherapeutic agents starting with radiolabelled platinum metal (which is expensive) results in a high cost of the radiolabelled chemotherapeutic agent and the possibility of insufficient dose being available for treatment of a patient. Similarly, unreliability of prior art synthetic methods and the occurrence of failures is totally unsatisfactory in a clinical context.

Still further, the "hot cell" facilities required for die synthesis of a radiolabelled chemotherapeutic such as cisplatin are expensive and there are significant economic benefits to be gained from a shortened synthesis, permitting greater throughput in the hot cell.

There is therefore a need for a shortened and more reliable method of synthesis of radiolabelled platinum based chemotherapeutic agents.

The present invention seeks to provide methods of synthesis of radiolabelled platinum based chemotherapeutic agents which provide a decrease in the synthesis time compared to previously known methods, and improved, more reliable yields, thereby allowing greater scope diagnostic, therapeutic and related applications.

The present invention also seeks to provide methods of incorporation of radionuclides such as $^{195m}Pt$ with both an imageable and a therapeutic emission into platinum based chemotherapeutic agents to facilitate use of the resultant radiolabelled agent (a) to determine the appropriate dosage of the chemotherapeutic agent in a patient, and/or (b) to determine the effectiveness of the chemotherapeutic agent in a patient, and/or (c) as a monitor of drug resistance and/or (d) to enhance cytotoxic effects by exploiting synergistic cytotoxic drug-radiation interactions.

SUMMARY OF THE INVENTION

Throughout the specification, unless the context clearly indicates otherwise, the words "comprise", "comprises", "comprising" or other variations thereof shall be understood as meaning that the stated integer is included and does not exclude other integers from being present even though those other integers are not explicitly stated.

In accordance with a first embodiment of the present invention, there is provided a method of synthesis of a radiolabelled platinum chemotherapeutic agent comprising the steps of:

a) converting a metal halide to a radiolabelled platinum halide wherein the radiolabel is a radioisotope of Pt; and b) synthesising the radiolabelled platinum chemotherapeutic agent from the radiolabelled platinum halide.

In accordance with a second embodiment of the present invention, there is provided a method of synthesis of cisplatin or carboplatin comprising the steps of:

a) converting a metal chloride to radiolabelled $PtCl_2$ wherein the radiolabel is a radioisotope of Pt; and b) synthesising cisplatin or carboplatin from the radiolabelled $PtCl_2$.

In accordance with a third embodiment of the present invention, there is provided a radiolabelled platinum chemotherapeutic agent produced by the method of synthesis of the first or second embodiments of the present invention.

In accordance with a fourth embodiment of the present invention, there is provided a method of assessing the effectiveness of treatment of a disease such as cancer wherein said treatment comprises administration of a platinum chemotherapeutic agent to a subject, which method comprises the steps of administering to said subject said platinum chemotherapeutic agent which is a radiolabelled platinum chemotherapeutic agent of the third embodiment of the present invention, in an amount sufficient to permit uptake or clearance of said radiolabel to be monitored in said subject and monitoring said subject.

In accordance with a fifth embodiment of the present invention, there is provided a method of diagnosis of a disease such as cancer in a subject comprising the steps of administering an effective amount of a radiolabelled platinum chemotherapeutic agent of the third embodiment of the present invention to said subject and monitoring said subject.

In accordance with a sixth embodiment of the present invention, there is provided a method of therapy of a disease such as cancer in a subject comprising the steps of administering an effective amount of a radiolabelled platinum chemotherapeutic agent of the third embodiment of the present invention to said subject.

In accordance with a seventh embodiment of the present invention, there is provided a method of prognosis of a disease such as cancer in a subject comprising the steps of administering an effective amount of a radiolabelled platinum chemotherapeutic agent of the third embodiment of the present invention to said subject and monitoring said subject.

In accordance with an eighth embodiment of the present invention, there is provided a use of a radiolabelled platinum chemotherapeutic agent of the third embodiment of the present invention in the preparation of a medicament for diagnosis, prognosis, therapy or assessment of the effectiveness of treatment of a disease such as cancer.

In accordance with a ninth embodiment of the present invention, there is provided a radiolabelled platinum chemotherapeutic agent of the third embodiment of the present invention when used in diagnosis, prognosis, therapy or assessing the effectiveness of treatment of a disease such as cancer.

Whilst the methods of the fourth to seventh embodiments are typically provided in relation to cancer, they are also applicable to other diseases which are able to be treated by platinum based chemotherapeutic agents.

DETAILED DESCRIPTION OF THE INVENTION

Usually, in the method of synthesis of the radiolabelled platinum chemotherapeutic agent the step of converting the metal halide into a radiolabelled platinum halide is carried out in a nuclear reactor or a cyclotron. Typically this conversion step is carried out by irradiation with neutrons in a nuclear reactor. The radiolabelled platinum halide may be a Pt(II) halide or a Pt(IV) halide. More typically, the present invention involves irradiating a Pt(II) halide, even more typically $PtCl_2$, with neutrons in a nuclear reactor. Alternatively, the metal halide may be the halide of a metal such as gold, iridium, etc. which can be converted into platinum by bombardment with protons, deuterons, alpha particles or other species in a cyclotron. In a typical embodiment, the radiolabelled platinum halide is a Pt(II) halide which is converted to cisplatin or carboplatin.

The platinum radioisotope in the synthetic method of the first or second embodiments is typically selected from the group consisting of $^{195m}Pt$, $^{197m}Pt$, $^{197}Pt$, $^{191}Pt$, $^{193m}Pt$ and mixtures thereof. Still more typically, the radioisotope is $^{195m}Pt$ or $^{193m}Pt$. Yet still more typically, the radioisotope is $^{195m}Pt$.

The radioisotopes of platinum may be prepared by methods which are generally known in the art. For example, radioactive halides of platinum which incorporate $^{193m}Pt$, $^{195m}Pt$ or $^{197}Pt$ may be prepared by irradiating a halide of $^{192}Pt$, $^{194}Pt$ and $^{196}Pt$, respectively (in oxidation state II or IV) with neutrons in a nuclear reactor. It will appreciated that the irradiation time to achieve a predetermined specific activity will be dependent on the nuclear reactor flux. Those versed in the art will readily determine the appropriate irradiation time for a given facility's flux.

It will be appreciated that when the platinum chemotherapeutic agent is a Pt(IV) species, the method of the present invention will usually include the steps of converting a metal halide to a radiolabelled Pt(IV) halide and synthesising the radiolabelled platinum chemotherapeutic agent from the radio label led Pt(IV) halide.

Typically, the platinum chemotherapeutic agents are selected from platinum coordination compounds which show cytotoxic properties and still more typically are platinum coordination compounds which show activity against cancer cells. The substituents on the platinum coordination compounds way be selected from the group consisting of $NH_3$, cyclic amino, alkylamino, arylamino, cycloalkylamino, aralkylamino, halo (especially chloro), hydroxy, alkoxy, carbarnate, carbonate ester, carboxylate, sulfate, sulfonate, phosphate, phosphonate, nitrate and bi-dentate ligands such as dicarboxylate, sulphate, phosphate or nitrate.

These platinum coordination compounds may be selected from platinum(II) and platinum (IV) coordination compounds and comprise those platinum(II) and platinum (IV) compounds with substituents in both the cis and trans configurations.

Still more typically, the platinum compounds are of the following general formulae (I) and (II);

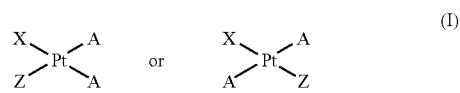

-continued

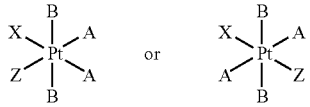
(II)

where each A is independently selected from halo (especially chloro), hydroxy, alkoxy and carboxylate or in which two A ligands together form a bi-dentate ligand such as di-carboxylate, sulphate, nitrate or phosphate;

each B, which may be the same or different, is selected from halo, hydroxy, carboxylate, carbarnate and carbonate ester;

Z and X are independently $NH_3$, cyclic amine, alkylamino, arylamino, cycloalkylamino, and aralkylamino, or Z and X together are $H_2N-Q-NH_2$ wherein Q is a divalent moiety selected from alkylene, cycloalkyl, aryl and aralkyl.

Typically the complex is of formula I.

In one embodiment, Z is a cyclic amine, where the ring may contain one or more other heteroatoms, which may be farther substituted, typically by substituents on the atom adjacent to the amine nitrogen atom. The cyclic amine may be a 5- or 6-membered monocyclic or 8 to 10-membered polycyclic, especially bicyclic, amine for example including a fused ring system where the amine is coordinated through the nitrogen atom of a pyridine ring. In the case of such bicyclic fused ring systems, the other ring may be phenylene or may contain one or more heteroatoms, especially nitrogen or oxygen. Typically the cyclic amine is an unsaturated amine, more typically pyridine.

In the case of substituted cyclic amines, the substituent may be alkyl of 1 to 6 carbon atoms or alkoxy of 1 to 4 carbon atoms (especially methyl or methoxy), nitro, halo (especially chloro or bromo), aryl or aralkyl (especially benzyl). The substituent may itself be substituted by halogen. The cyclic amine may carry other substituents either adjacent to the coordinating nitrogen atom or elsewhere on the ring.

Typically, in formula (I) or (II) each A is the same, and is more typically chloro, or together two A ligands, when present, form cyclobutane-1,1-dicarboxylate or sulphate. In the case of Pt(IV) complexes of formula II, typically each B is the same, and more typically is hydroxy.

More typically, the platinum coordination compounds are selected from cisplatin, carboplatin and other platinum malonato coordination compounds. The term "malonato compounds" is understood to mean those platinum coordination compounds that comprise in their structure a $(-OOC)_2-C<$ linkage. Still more typically, die chemotherapeutic agent is carboplatin or cisplatin, and yet more typically cisplatin.

Examples of platinum chemotherapeutic agents are described in U.S. Pat. Nos. 3,904,663, 4,115,418, 4,137,248, 4,140,707, 4,169,846, 4,203,912, 4,225,529, 4,230,631, 4,256,652, 4,271,085, 4,329,299, 4,431,666, 4,466,924, 4,560,781, 4,562,275, 4,575,550, 4,578,491, 4,584,316, 4,584,392, 4,599,352, 4,614,811, 4,658,047, 4,661,516, 4,665,210, 4,670,458, 4,675,336, 4,680,308, 4,687,780, 4,720,504, 4,739,087, 4,758,588, 4,760,155, 4,760,156, 4,760,157, 4,845,124, 4,861,905, 4,968,826, 5,011,959, 5,041,578, 5,194,645, 5,244,919, 5,288,887, 5,393,909, 5,434,256, 5,519,155, 5,665,771 and 6,008,395, which also describe the synthesis of these agents from platinum(II) or platinum(IV) halides or from substances which can be synthesised therefrom by well-known reactions. The disclosure of the above referenced United States patents is incorporated herein by reference.

Typically, in the methods of the forth, fifth and seventh embodiments, the step of monitoring the subject includes the step of monitoring the uptake of the platinum radiolabelled chemotherapeutic agent in the subject, typically in a localised area of the subject. Still more typically, the step of monitoring is achieved by imaging means. Additionally or alternatively the step of monitoring the subject may further comprise the step of monitoring the clearance of the radiolabelled chemotherapeutic agent from the subject.

Still more typically in the methods of the fourth, fifth and seventh embodiments, the step of monitoring the subject comprises monitoring relative uptake of the radiolabel in target and non-target organs to allow determination in the subject of the relative toxicity of the chemotherapeutic agent. Typically, the monitoring process seeks a high target to non-target ratio. For example, if a patient is compromised in the excretory organs (i.e. kidneys are not functioning properly) then the monitoring step allows a reassessment of the dosage to be provided to the subject. Hence, in cases where the target organs have relatively high uptake of the chemotherapeutic agent, the uptake in non-target organs should also be considered in the determination of the correct dosage. However, the critical factor is still whether the chemotherapeutic agent is absorbed in the target region.

In a typical application of a method of the fourth embodiment, a patient is diagnosed with some form of cancer by standard methods e.g CT, MRI, X-ray and biopsy, and is referred for chemotherapy by administration of cisplatin. Although it is clearly important for the patient to receive the appropriate dose, in current therapies the clinician will typically live estimates of an appropriate dose, but will be unsure whether the patient will experience severe or mild side effects. The use of radiolabelled product prepared by the method of the present invention can provide the clinician with information on how the cisplatin distributes in that particular patient which can be used to more effectively prescribe the appropriate dose. Additionally, if monitoring of uptake indicated that the product was going to take longer than desired to clear from the kidneys, a clearing agent could be administered. Further, knowledge of whether the product is taken up well by the target (cancer) assists the clinician in the choice of the appropriate drug for treatment. That is, the clinician can determine whether cisplatin is likely to be effective or whether some other chemotherapeutic agent is indicated. Where the patient presents for a second treatment the method of the fourth embodiment can be used to establish if the product is still effective (that is, whether it is still taken up at the target site and is clearing well from excretory organs.)

A method of assessment of the effectiveness of a treatment of a disease in accordance with the fourth embodiment of the invention typically comprises the steps of monitoring the selectivity of uptake of the platinum radiolabelled chemotherapeutic agent in a localised area of the subject which is the site of the disease, in order to determine the effectiveness of the platinum chemotherapeutic agent against the disease. The method of assessment can allow continuous monitoring at selected time intervals by imaging the platinum radiolabelled chemotherapeutic agent so as to determine the presence or absence of cancer cells in tissue. Typically, in this method, over a certain period of time, the localisation of the platinum chemotherapeutic agent within the diseased tissue can be monitored in a particular subject. By monitoring the platinum radiolabelled chemotherapeutic agent in the subject it may be determined whether there is any resistance to the particular chemotherapeutic agent or whether the chemotherapeutic agent is effective against the disease.

Typically, the method of assessment will further comprise a step of determining the extent of any cancer cells in the subject by monitoring the increase or reduction of cancer cells in the subject over time.

Thus the method of assessment permits assessing drug resistance in a subject after administration of the platinum radiolabelled chemotherapeutic agent. If the subject shows over a period of time that the number of cancer cells is not being reduced, or that the particular tissue does not retain the chemotherapeutic agent, then an alternative therapy may be instigated, such as administration of other chemotherapeutic agents and/or external radiation.

More typically, the method of assessment further comprises the step of administering a composition of a mostly unradiolabelled or "cold" platinum chemotherapeutic agent with an amount of the radiolabelled chemotherapeutic agent to a subject. The composition of the two components is blended in a known ratio. Typically, the proportion of the radiolabelled chemotherapeutic agent to the unradiolabelled therapeutic agent is 5 to 8 percent (5 to 8 mg of radiolabelled chemotherapeutic agent with 100 mg of the "cold" chemotherapeutic agent). The administration of this composition allows assessment of the selective uptake of a particular platinum chemotherapeutic agent by detection of the radiolabelled platinum chemotherapeutic agent in the said subject, particularly a localised area of said subject.

A method of diagnosis of the fifth embodiment and a method of prognosis of the seventh embodiment will typically comprise the step of monitoring the selective uptake of the radiolabelled chemotherapeutic agent throughout the subject in order to determine the presence or absence of a disease or extent of disease. The method of diagnosis or method of prognosis will typically comprise administration of a platinum radiolabelled chemotherapeutic agent which has been radiolabelled with a radionuclide having imaging culpability. More typically, the radiolabelled chemotherapeutic agent will allow the detection and tracking of the platinum chemotherapeutic agent throughout the subject by use of imaging means. The imaging step will determine the presence of, or extent of, disease throughout the subject by identifying cancer cells in the subject after uptake of the chemotherapeutic agent. This is shown by localisation of the radiolabelled chemotherapeutic agent in a particular subject.

A method of therapy in accordance with the sixth embodiment of the invention typically comprises the administration of a composition of a radiolabelled chemotherapeutic agent which has a therapeutic level of radioactivity and emission. Typically, in this method the radiolabelled platinum chemotherapeutic agent emits an auger or beta emission which acts to split the DNA of cancer cells. The auger or beta emission can thus act to enhance the chemotherapeutic properties of the radiolabelled platinum chemotherapeutic agent.

It is to be understood that the term "effective amount" for each of the method of diagnosis, prognosis, assessment or therapy shall vary and depend upon the particular requirements of each method. It is expected that these "effective amounts" shall vary depending on a number of factors including the selected cancer, tissue and particular requirements of the subject. Given the teaching herein, clinicians applying the methods of the present invention will have no difficulty in determining effective amounts of radiolabelled platinum chemotherapeutic agents.

A further application of compounds of the third embodiment is in risk assessment, especially of newly developed candidate chemotherapeutic agents containing platinum. In such an application, a method of the first embodiment provides the chemotherapeutic agent containing a radiolabel, whose distribution and uptake in an animal can be assessed much more readily than can the distribution and uptake of the corresponding unradiolabelled substance. The use of the radiolabelled substance allows dynamic studies to be performed which readily provide more accurate information for determining pharmacokinetics of the substance.

DESCRIPTION OF PREFERRED EMBODIMENTS

In Scheme 1, there is shown in schematic form a prior art process for producing radiolabelled cisplatin from Pt metal. This process comprises irradiating enriched $^{194}$Pt metal in a high flux nuclear reactor (designated 'HIFAR' in the Schemes). The irradiated $^{194}$Pt is then treated with aqua regia (HCl/HNO$_3$) to form H$_2$PtCl$_6$, H$_2$PtCl$_6$ is then treated with NaCl to form Na$_2$PtCl$_6$ which in turn is reacted with hydrazine to form Na$_2$PtCl$_4$, Na$_2$PtCl$_4$ is reacted with KI to form K$_2$PtI$_4$, which is converted to Pt(NH$_3$)2I$_2$ reaction with NH$_4$OH. Pt(NH$_3$)$_2$I$_2$ is reacted with AgNO$_3$ to form Pt(NH$_3$)$_2$ (H$_2$O)$_2$(NO$_3$)$_2$which is then reacted with HCl to form cisplatin. The synthesis time from conclusion of irradiation of $^{194}$Pt to formation of cisplatin is typically approximately 6.5 hours and in 21 replicate experiments the yield ranged from 0 to 30% with an average yield of 8.4%. Six of these replicates gave zero yield.

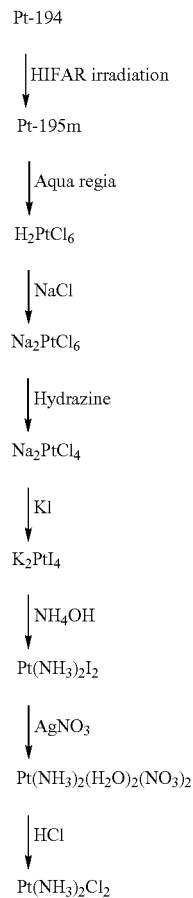

Scheme 1

In Scheme 2, there is shown in schematic form a process according to the present invention for producing cisplatin. Enriched Pt-194 metal is treated with aqua regia (HCl/

HNO$_3$) to form H$_2$PtCl$_6$, H$_2$PtCl$_6$ is subjected to thermal decomposition via a furnace to form Pt(II)Cl$_2$. Pt(II)Cl$_2$ is then subjected to irradiation in a high flux nuclear reactor and reacted with KI to form K$_2$PtI$_4$, which is converted to cisplatin by the same steps as described above. The synthesis time from conclusion of irradiation of PtCl$_2$ to formation of cisplatin is typically about 1.5 hours and in ten replicates the yield ranged from 56.7 to 61.6%, averaging 60.1%.

Scheme 2

Pt-194

↓ Aqua regia

H$_2$PtCl$_6$

↓ Thermal decomposition

PtCl$_2$

↓ HIFAR irradiation $^{195m}$PtCl$_2$

↓ KI

K$_2$PtI$_4$

↓ NH$_4$OH

Pt(NH$_3$)$_2$I$_2$

↓ AgNO$_3$

Pt(NH$_3$)$_2$(H$_2$O)$_2$(NO$_3$)$_2$

↓ HCl

Pt(NH$_3$)$_2$Cl$_2$

Scheme 3 shows in schematic form a process according to the present invention for producing carboplatin. In this process. Pt(II)Cl$_2$ radiolabelled with $^{195m}$Pt is prepared in the same way as described above with reference to Scheme 2 and converted to K$_2$PtI$_4$ as described above with reference to Scheme 2. Conversion of the radiolabelled K$_2$PtI$_4$ to radiolabelled carboplatin involves the steps of treating the K$_2$PtI$_4$ with NH$_4$OH to produce Pt(NH$_3$)$_2$I$_2$ and converting this to carboplatin by reaction with silver cyclobutanedicarboxylate (AgCBCDA). The synthesis time from conclusion of irradiation of PtCl$_2$ to formation of carboplatin is typically about 1.75 hours.

Scheme 3

Pt-194

↓ Aqua regia

-continued

H$_2$PtCl$_6$

↓ Thermal decomposition

PtCl$_2$

↓ HIFAR irradiation $^{195m}$PtCl$_2$

↓ KI

K$_2$PtI$_4$

↓ NH$_4$OH

Pt(NH$_3$)$_2$I$_2$

↓ AgCBDCA

Pt(NH$_3$)$_2$CBDCA

EXAMPLES OF THE INVENTION

The following examples serve to illustrate the invention and should not be construed as limiting the generality of the above description.

Example 1

Preparation of PtCl$_2$

Conversion of Pt(0) to Pt(IV)

Enriched Pt-194 metal (>95%; 359 mg) was digested in ~2 mL aqua regia at 120° C. with a N$_2$ stream above the solution. The solution was heated until it turned dark orange (approximately 20 minutes). The solution was transferred to another glass tube and evaporated to dryness under N$_2$ on the hotplate. A further 2 ml of arma regia was added to the original tube containing the Pt metal and this process was repeated until all the metal was digested. The solutions were combined and evaporated to dryness under N$_2$. The residue was further digested with approximately 1 mL concentrated HC and evaporated to dryness under N$_2$ to yield H$_2$PtCl$_6$.

Thermal Decomposition

The H$_2$PtCl$_6$ (0.40 gm) was transferred to a ceramic boat and decomposed to PtCl$_2$ by heating in a furnace over a range of temperatures from 20–300° C. over a 2 hr period in the presence of air. The resultant PtCl$_2$ powder was characterised by x-ray crystallography. Recovery of PtCl$_2$ product was >90% of theoretical yield, based on Pt metal.

Example 2

Synthesis of [$^{195m}$Pt]Cisplatin

Approximately 60 mg of PtCl$_2$ is irradiated for at least 8 days in a high flux nuclear reactor. Once irradiation is complete the [$^{195m}$Pt]PtCl$_2$ (54.98 mg) is transferred to a kimble tube and then suspended in 100 μl of a solution of 0.1 M HCl. To this mixture is then added 300 μl of 4 M KI followed by 100 μl of concentrated ammonia. A yellow precipitate forms [(NH$_3$)$_2$PtI$_2$] and the solution becomes brown. The mixture is gently warmed in a 50° C. water bath for approximately 5 minutes. The mixture is then centrifuged for 3 minutes at 6000 rpm and the supernatant is transferred to another test tube. The precipitate is washed with 800 μl of 0.01 M KI and centrifuged for 3 minutes at 6000 rpm. To the first supernatant another 28 μl of concentrated ammonia is added to ensure all the (NH$_3$)$_2$PtI$_2$ has precipitated, and the solution is warmed for 5 minutes in a 50° C. bath. The resulting mixture is centrifuged for 3 minutes at 6000 rpm, the supernatant is removed and the precipitates combined using 400 μl 0.1 M KI. To the resultant mixture of (NH$_3$)$_2$PtI$_2$ in 0.1 M KI is then added 0.4 M AgNO$_3$ (1.1 mL) slowly to form (NH$_3$)$_2$Pt(H$_2$O)$_2$(NO$_3$)$_2$. This time a pale yellow precipitate forms (AgI) and the solution becomes clear. The mixture is centrifuged for 3 minutes at 6000 rpm and the supernatant is removed. The remaining AgI is washed with 800 μl of 0.01 M NaNO$_3$ and the supernatants are combined. To remove any remaining Ag$^+$, 140 μL of 1.0 M HCl is added to the supernatant and the white precipitate is removed after centrifugation (3 minutes/6000 rpm). A final test for the presence of any Ag$^+$ is done by adding a further 40 μL of 1.0 M HCl. If no precipitate forms 400 μL of concentrated HCl is added and the solution is heated for 5 minutes at 50° C. The solution becomes a clear yellow and a yellow precipitate forms, which is [$^{195m}$Pt]cisplatin. The yellow precipitate is collected by filtration and washed with chilled ethanol and acetone (2 mL). Yield 43.3 mg (70%). The precipitate is then dissolved in 40 mL of saline. The solution is monitored by UV/V is spectroscopy and the purity of the product is determined by calculating the ratio of absorbance at 301 and 365 nm to be 5.4±0.2. Gamma Spectrometry showed radionuclidic purity to be >95% and final specific activity to be 4.0 MBq/mg.

Example 3

Synthesis of [$^{195m}$Pt]Carboplatin

Starting with 62.14 mg of [$^{195m}$Pt]PtCl$_2$ prepared as described above, the synthesis of [$^{195m}$Pt]carboplatin is similar to that described above except for the following changes. The kimble tube containing the mixture of (NH$_3$)$_2$PtI$_2$ in 0.1 M KI is covered in aluminum foil to prevent light from entering, and then 45 mg of silver cyclobutanedicarboxylate is added followed by 800 μL of water. The mixture is then sonicated at 50° C. for 20 minutes in the dark and centrifuged for 3 minutes at 6000 rpm. The supernatant is transferred to a 50 mL beaker and approximately 30 mL of chilled acetone is added. The mixture is left in the fridge at about 5° C. overnight or 30 minutes at −4° C. The clear crystals of [$^{195m}$Pt]carboplatin which form are filtered off and dried under vacuum. Yield 29.45 mg (33.95%). The product is then dissolved in saline and the chemical and radionuclidic purity is checked by HPLC and gamma spectrometry. The final product has a chemical and radionuclidic purity >95%. Specific activity of the final product is >3 MBq/mg.

Example 4

Pilot Clinical Study

This Example illustrates the usefulness of radiolabelled platinum based chemotherapeutic agents in predicting the likely response of a patient to treatment by non-radiolabelled platinum based chemotherapeutic agents and hence the role of the radiolabelled agents as prognostic indicators for the patient outcome.

As part of a pilot study to evaluate the use of $^{195m}$Pt-Cisplatin and $^{195m}$Pt Carboplatin for prognosis of cancer, two patients were injected with $^{195m}$Pt-Cisplatin prepared as described in Example 2.

Patient No. 1 had oesophageal cancer, with one large lesion in the mediastinal region and large metastases in the liver. F-18-DG imaging confirmed the presence of both lesions. The patient was injected with $^{195m}$Pt-Cisplatin (100 MBq; specific activity 4.2 MBq/mg cisplatin) and imaged over a 5 day period. This patient showed negligible uptake of the radiolabelled cisplatin in both lesions. The patient was placed on a normal cisplatin chemotherapy in combination with radiation. After 2 months no evidence of response to treatment was noted.

Patient No. 2 had oesophageal cancer. CT confirmed a large lesion in the mediastinal region. The patient was injected with $^{195m}$Pt-Cisplatin (50 MBq: specific activity 3.6 MBq/mg cisplatin) and Imaged over a 3 day period. The images showed significant uptake of the $^{195m}$Pt-Cisplatin in the mediastinal region. The patient has undergone cisplatin chemotherapy and is being monitored for response to treatment.

The two patient studies show significant difference in uptake of $^{195m}$-Pt-Cisplatin illustrating the potential of the agent to assist in selecting patients that ate most likely to respond to cisplatin chemotherapy.

The images obtained after administering radiolabelled platinum based chemotherapeutic agents can also be used to monitor uptake in and clearance from non-target organs (for example liver and kidneys). Information obtained regarding clearance rates can be used to assist in estimation of the appropriate dose of the cisplatin chemotherapeutic for individuals. The ability to predict the type and extent of side effects has a role in minimising irreversible damage caused by an over-estimation of chemotherapeutic agent.

The advantages of the invention reside in a reduced synthesis time of approximately 1.5 h for cisplatin and 1.75 h for carboplatin, as well as higher and more reliable yields (greater than 50%) and reduced risk of a failed synthesis (estimated at less than approximately 1%.)

Modifications and variations such as would be apparent to a skilled addressee are deemed to be within the scope of the present invention. It is to be understood that the present invention is not limited to the particular embodiment(s) described above.

The invention claimed is:

1. A method of synthesis of a radiolabelled platinum chemotherapeutic agent comprising the steps of:
(a) thermally decomposing a hydrohalide salt of platinum (II) or a hydrohalide salt of platinum(IV) to give a platinum(II) halide or a platinum(IV) halide;
(b) converting the platinum(II) halide to a radiolabelled platinum(II) halide, or converting the platinum(IV) halide to a radiolabelled platinum(IV) halide wherein the radiolabel is a radioisotope of Pt; and
(c) synthesising the radiolabelled platinum chemotherapeutic agent from the radiolabelled platinum halide; wherein said radiolabelled platinum chemotherapeutic agent is selected from compounds of the general formulae (I) and (II):

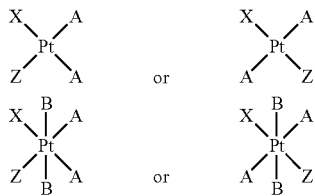

where each A is independently selected from halo, hydroxy, alkoxy and carboxylate or in which two A ligands together form a bi-dentate ligand;

each B, which may be the same or different is selected from halo, hydroxy, carboxylate, carbamate and carbonate ester;

Z and X are independently $NH_3$, cyclic amine, alkylamino, arylamino, cycloalkylamino, and aralkylamino, or Z and X together are $H_2N-Q-NH_2$ wherein Q is a divalent moiety selected from alkylene, cycloalkyl, aryl and aralkyl.

2. A method according to claim 1 wherein said platinum (II) halide is $PtCl_2$ or said platinum(IV) halide is $PtCl_4$.

3. A method according to claim 1 wherein said radiolabelled platinum chemotherapeutic agent is of formula I.

4. A method according to claim 1 wherein each A is the same and is chloro, or wherein two A ligands, taken together, form cyclobutane-1,1-dicarboxylate or sulfate.

5. A method according to claim 1 wherein said platinum chemotherapeutic agent is cisplatin or carboplatin.

6. A method according to claim 1 wherein said radiolabelled platinum(II) halide is $PtCl_2$ or said radiolabelled platinum(IV) halide is $PtCl_4$.

7. A method of synthesis of cisplatin or carboplatin comprising the steps of:
a) thermally decomposing a hydrohalide salt of platinum (II) or platinum(IV) to give $PtCl_2$;
b) converting $PtCl_2$ to radiolabelled $PtCl_2$ wherein the radiolabel is a radioisotope of Pt; and
c) synthesising cisplatin or carboplatin from the radiolabelled $PtCl_2$.

8. A method according to claim 1 wherein step (a) comprises thermally decomposing a hydrohalide salt having the formula $H_2PtX_6$, wherein X is a halide, to give a platinum(II) halide or a platinum(IV) halide.

9. A method according to claim 1 wherein step (a) comprises thermally decomposing a hydrohalide salt having the formula $H_2PtCl_6$, to give a compound selected from the group consisting of $Pt(II)Cl_2$ and $Pt(IV)Cl_4$.

10. A method according to claim 1 wherein step (a) comprises thermally decomposing a hydrohalide salt having the formula $H_2PtX_6$, wherein X is a halide, to give a platinum(II) halide.

11. A method according to claim 1 wherein step (a) comprises thermally decomposing $H_2PtCl_6$ to give $Pt(II)Cl_2$.

12. A radiolabelled platinum chemotherapeutic agent produced by the method of synthesis of any one of the claims 1–6, 7, and 8–11.

13. A method of assessing the effectiveness of treatment of cancer wherein said treatment comprises administration of a platinum chemotherapeutic agent to a subject, which method comprises the steps of administering to said subject a platinum chemotherapeutic agent according to claim 12 in an amount sufficient to permit uptake or clearance of said radiolabel to be monitored in said subject, and monitoring said subject.

14. A method of diagnosis of cancer in a subject comprising the steps of administering an effective amount of a platinum chemotherapeutic agent according to claim 12 to said subject and monitoring said subject.

15. A method of therapy of cancer in a subject comprising the steps of administering an effective amount of a platinum chemotherapeutic agent according to claim 12 to said subject.

16. A method of prognosis of cancer in a subject comprising the steps of administering an effective amount of a platinum chemotherapeutic agent according to claim 12 to said subject and monitoring said subject.

* * * * *